United States Patent [19]

Mosier

[11] 4,438,209

[45] Mar. 20, 1984

[54] RADIOIMMUNOASSAY FOR FIBRINOPEPTIDE A

[75] Inventor: Larry D. Mosier, St. Louis, Mo.

[73] Assignee: Mallinckrodt, Inc., St. Louis, Mo.

[21] Appl. No.: 284,152

[22] Filed: Jul. 17, 1981

[51] Int. Cl.$^3$ .................... G01N 33/56; G01N 33/58; G01N 33/60

[52] U.S. Cl. .................................. 436/542; 436/804; 436/825; 436/826

[58] Field of Search ............... 436/542, 804, 825, 826; 424/1

[56] References Cited

PUBLICATIONS

Kettner et al., The Chemistry and Biology of Thrombin, pp. 129-141.
Budzynski et al., Thrombos. Diathes, (1975) 34: 709-717.
Kettner et al., Thrombosis Res. 14: 969-973 (1979).
Hauptmann et al., Thrombosis Res., 20: 347-351 (1980).
Budzynski et al., Pol. Arch. Med. Wewn, 1978, 42-48.
Gerris et al., Thrombosis Res. 5: 197-212 (1974).
Bynum et al., Arch. Int. Med. 137 (1977) 1385-89.
Wilner, Thrombosis Res. 15:601-610 (1979).
Nossel et al., Thrombosis Diathes., (1975) 33:426-34.
Nossel et al. J. Clin. Investigation, 54: 43-53 (1974).
Kockum et al., Throm. Res., 19: 589-98 (1980).
FPA Package Insert, Mallinckrodt, Dated 7/29/81.
Cronlund et al., J. Clin. Invest., 58(1976) 142-151.

*Primary Examiner*—Christine M. Nucker
*Attorney, Agent, or Firm*—R. J. Klostermann; L. N. Goodwin; G. J. Fishel

[57] ABSTRACT

Radioimunoassay methods for determining the concentration of fibrinopeptide A in plasma, anticoagulation reagents for use in such methods and package test kits containing the reagents for use in such methods are provided.

11 Claims, No Drawings

RADIOIMMUNOASSAY FOR FIBRINOPEPTIDE A

This invention relates to radioimmunoassay (RIA) methods for determining the concentration of Fibrinopeptide A (hereinafter sometimes referred to as FPA) in plasma, to anticoagulant reagents utilized in such methods and to packaged test kits containing the reagents utilized in such methods.

Currently, there is an increased interest in assays for measuring various substances in the coagulation system. Measurement of one of these substances, FPA, will give an indication of hypercoaguability. A series of events in the coagulation system results in the action of thrombin on fibrinogen causing the release of FPA as the first event in the process. Further action causes the release of Fibrinopeptide B resulting in a fibrin monomer which polymerizes into an insoluble clot with the aid of another enzyme.

Laboratory tests presently used for the determination of FPA are inadequate. One such RIA test developed by H. L. Nosel, is described in Measurement of FPA in Human Blood, J. Clin. Invest. 54: 43–53 (1974) and Potential Use of FPA Measurements in the Diagnosis and Measurement of Thrombosis, Thrombos, Diathes, haemorrh. (Stuttg) 33: 426 (1975) both of which are incorporated herein by reference. This test is capable of detecting less than 2 ng of FPA per ml. of plasma which corresponds to the in vivo conversion of about 200 ng (about 0.09%) of the normal circulating fibrinogen. However, sample collection and handling are very critical and false elevations of FPA levels are often seen.

It is an object of this invention to provide a RIA procedure for FPA in plasma that provides consistent and reliable results.

In accordance with this invention, there is provided an improvement in the competitive RIA process for determining the in vitro concentration of FPA in plasma wherein first a sample of blood is collected. Then the thrombin in said sample is inhibited by an inhibiting amount of a thrombin inhibitor and plasma is separated from said sample. Next, a sample of said plasma is contacted under radioimmunoassay competitive binding conditions with a sufficient amount of antibody to FPA and radioactively labeled FPA, thereafter antibody bound FPA is separated from unbound FPA and radioactivity measured. The improvement involves using certain inhibitors to inhibit the thrombin.

Another embodiment of the invention is directed to anticoagulant reagents for use in the RIA methods which contain one of the inhibitors, a chelating agent and an antiproteolytic agent.

Another aspect of this invention is directed to packaged test kits containing the reagents utilized in such RIA methods.

The thrombin inhibitors that may be used in the practice of this invention are those that are fast acting, i.e., inhibit thrombin almost instantaneously, e.g., less than 10 seconds; stable in plasma, i.e., permit formation of little or no FPA; stable for extended periods, i.e. have normal shelf lifes, prior to use; and essentially irreversible inhibitors of thrombin. One such inhibitor is D-phenylalanyl-L-prolyl-L-N-[2-(1-chloro-7-guanidoheptane-2-one)] (hereinafter referred to as D-Phe-Pro-ArgCh$_2$Cl) and suitable salts thereof, e.g., any salt which will inhibit thrombin and have the aforementioned properties, that is, fast acting, stable in plasma, etc.

Suitable salts include the acid addition salts derived from any strong or weak inorganic or organic acid. Suitable inorganic acids include halogen containing acids such as hydrochloric, hydrofluoric or hydrobromic; phosphorus containing acids such as phosphoric, phosphorus, or hypophosphorus; sulfur containing acids such as sulfuric, hyposulfurous, or thiosulfuric; and others such as nitric, or manganic. Suitable organic acids include formic, acetic, chloroacetic, citric, lactic, tartaric and the like.

The acid addition salts are prepared either by dissolving the free base in an aqueous solution containing the appropriate acid and isolating the salt by evaporating the solution or by reacting the free base and the selected acid in an organic solvent, in which case the salt separates directly or can be obtained by concentration of the solution. If two or more equivalents of acid are used, a poly-acid addition salt is obtained, in those instances where there is more than one basic nitrogen atom in the molecule. If one equivalent of acid is used a mono-acid addition salt is obtained.

The HF acid addition salt and the free base of D-Phe-Pro-Arg-Ch$_2$Cl can be prepared according to the procedure described in a recent publication by Ketner, Thrombosis Research 14: 969–993 (1979).

As mentioned the first step of the process of this invention involves collection of a blood sample, inhibiting the thrombin in said sample and separating the plasma from said sample.

A blood sample may be collected by the usual means, e.g., venipuncture using a 20 gauge needle. Generally, 5 to 10 ml of blood is collected.

The blood sample is simultaneously or immediately thereafter combined with an inhibiting amount of one of the aforementioned inhibitor to inhibit the thrombin in said sample. For example, an inhibiting amount is an amount of from about 0.01 mg to 1.0 mg, preferably from about 0.04 mg. to about 0.6 mg. per ml. of whole blood. Advantageously, by combining along with the inhibitor a chelating amount, e.g., from about 2 mg. to 6 mg., preferably from about 3.5 to 4.5 mg per ml. of whole blood of a chelating agent such as ethylenediaminetetraacetic acid (EDTA) or ethylene glycol bis(B-aminoethyl ether)N,N,N',N' tetraacetic acid (EGTA) or their salts in vitro thrombin generation is substantially or completely inhibited. Normally, an antiproteolytic agent to substantially reduce or prevent proteolysis of FPA is also added in an antiproteolytic amount, e.g., from about 50 to 300 KIU (Kallekrein inhibitor units) preferably from about 90 to 150 KIU per ml. of whole blood. Such agents include Trasylol ® (aprotinin). Advantageously, by using the chelating agent and the antiproteolytic agent along with one of the thrombin inhibitors of this invention, collection problems are significantly minimized and plasma samples are obtained which are stable at room temperature for several hours, e.g. 2 to 4; at 4° C. for several days, e.g. 1 to 3, and at −20° C. for several months, e.g. 2 to 4.

All three can be conveniently combined, advantageously, in an aqueous solution, e.g., sodium chloride or buffer solution to form an anticoagulant reagent. The anticoagulant reagent contains a sufficient amount of the inhibitor, chelating agent and antiproteolytic agent so each will perform its intended function on addition of the anticoagulant reagent to the blood. Normally, in each ml of an aqueous anticoagulant reagent from about 0.1 mg to about 1 mg, preferably from about 0.4 to about 0.6 mg of the inhibitor is present, from about 20 mg to about 60 mg, preferably from about 35 mg to about 45 mg of the chelating agent is present and from about 500 to about 3000, preferably from about 900 to about 1500 KIU/ml of the antiproteolylic agent is present. The reagent is utilized in an anticoagulant amount, for example an aqueous reagent is utilized in an amount of from about 0.05 to about 1 ml, preferably from about 0.1 to about 0.2 ml per ml of whole blood. The pH of the reagent is generally from about 4 to 7.

Next, the plasma is separated from the cells in the usual manner by centrifugation, e.g. at a 1,000 to 1500×g for a sufficient period of time, e.g., 20 minutes at 4° C. or room temperature. Preferably, this is done as soon as possible after collection. The separated plasma is stored at a suitable temperature, for example, 20° C. or lower until used in the RIA assay in accordance with this invention.

Before the plasma is used in the RIA procedure, normally, it must be pretreated to remove the cross-reactive fibrinogen and fibrin (ogen) fragments from the plasma. This can be done in the usual ways, for example, by alcoholic precipitation of plasma and dialysis of the filtrate or by the addition of bentonite or other similar acting materials to the plasma in an amount sufficient to reduce or remove the interfering material from the plasma. Normally, a slurry of bentonite is added to the mixture of plasma. The plasma is then mixed and centrifuged at a minimum of 1200×g for sufficient period of time, e.g., 20 minutes. The supernatant is removed and used in the assay procedure.

The second step of the process of this invention involves carrying out a RIA assay under RIA competitive binding conditions in the usual manner, for example, as described in the aforementioned NOSSEL publication. Basically, this involves adding a sufficient amount of an antibody to FPA and radioactively labelled FPA to the plasma sample, thereafter separating antibody bound FPA from unbound FPA and measuring the radioactivity.

Any radioactively labeled FPA which will react with the FPA antibody may be used. Conveniently, a radioactively labeled desaminotyrosyl-FPA complex may be utilized. It can be labeled, e.g. with I-125 or other radioisotopes using the chloramine T method. A detailed procedure for preparing this complex may be found in the aforementioned NOSSEL publication.

Generally, FPA is labeled with I-125 or other radioisotopes to a specific activity from about 800 microcuries per microgram to about 1600 microcuries per microgram. The radiolabeled FPA may be diluted as is known in the art to provide a radiolabeled reagent capable of ideal immunometric association with the antibodies in the reaction medium and optimum assay sensitivity. This dilution may be made with suitable aqueous buffers having a pH of from about 4 to 10. Examples of suitable buffers which may be employed for the dilution include Tris, a commercially available, aqueous solution containing Tris (hydroxymethyl) amino methane; barbital, a commercially available, aqueous solution of 5,5-diethylbarbituric acid, and other well-known buffers. The extent, if any, of the dilution may depend on the initial specific activity and the desire disintegrations per minutes (DPM) required to realize optimum counting and sensitivity of the assay.

After the unknown sample of plasma has been mixed with the radioactively labeled FPA reagent, an antibody, e.g., an antibody solution containing antibody capable of immunoreactivity with the FPA and radioactive FPA, is added to the mixture. The antibody has a specificity for the FPA and the radioactive FPA. Thus, the quantity of radioactive FPA bound by a given quantity of antibody is decreased in the presence of unlabeled FPA from the unknown plasma sample and the effect is directly related to the concentration of the unlabeled FPA.

Methods known in the art may be employed for obtaining the antibodies capable of reacting with the FPA and the labeled FPA. For example, the antibody may be prepared by innoculating a host animal, e.g. a rabbit. After innoculation, a period of time is allowed to elapse during which the host will develop antibody, whereupon the antiserum is bled from the animal to provide the antibody. The antibody may be diluted in a buffer material similar to that used for diluting the radiolabeled FPA to a concentration to obtain the maximum performance in the assay to provide a first antibody reagent. For example, it is preferred that the antiserum be diluted to the extent that 20 to 80%, preferably 30 to 70%, of a tracer quantity of radioactive FPA (0.01 to 0.09 Ci) is bound. Once the antibody has been added to the mixture of the plasma the resulted mixture is incubated at a temperature and for a sufficient period of time to produce substantial equilabration of antibody bound FPA and unbound FPA. During incubation, the antibody in diluted antiserum forms an immune complex with the radioactive FPA and FPA. In the practice of this invention, it is preferred that the incubation step be conducted at a temperature of about 15° to 37° C., preferably 20° to 30° C. for a period of approximately 40 to 120 minutes, preferably 40 minutes after which binding of the FPA by the antibody has been found to reach substantial equilibrium.

Upon completion of the incubation step, the unbound FPA is separated from the antibody bound FPA.

Separation is conveniently effected by the usual methods, including charcoal, or a relatively thin strip of a membrane consisting essentially of an ion exchange resin. Another separation technique is the use of a second antibody which is not specific to the FPA but is specific to the antibody (first antibody) which reacts with the FPA. The second antibody may be prepared by innoculating an animal different from the one in which the first antibody has been obtained, with gammaglobulin of a normal animal of the type from which the antibody has been obtained but not specific to the antigen to be assayed. The second antibody may also be diluted in a buffer material similar that used for diluting the radiolabeled antigen and first antibody reagents to a concentration to obtain the maximum performance in the assay.

To aid in the separation, polyethylene glycol or another suitable polymer may also be provided in the reaction medium by addition thereto as a separate reagent after or even before addition of the second antibody solution. It is preferred that all or a major portion of the polymer be provided in the reaction medium by prior incorporation into the second antibody reagent. Thus, typically from about 1% to 15% by weight, preferably about 3% to 12% by weight, say about 7 to 9% by weight of the polymer may be included in the second antibody reagent to provide a sufficient concentration of polymer in the reaction medium to accelerate an immuno precipitation reaction between the first water soluble antibody carrying radiolabeled or unlabeled antigen.

The RIA test protocol may vary, depending upon a number of factors. In general, however, the test reagents may all be equilibrated to room temperature, then appropriate quantities of standards, containing predetermined concentrations of FPA can be added to a series of tubes and a sample of plasma can be added to another series of tubes, labeled FPA reagent, and FPA antibody reagent can then be added sequentially to all of the tubes which are then vortexed, covered and incubated. If a second antibody is used for separation, it can next be added to the tubes. Typically, according to the invention, no incubation of the tubes is required after addition of the second antibody reagent although the tubes may be incubated if desired. The tubes are then vortexed and centrifuged. The tubes can be decanted and the supernatant liquid discarded. The tubes then can be counted and a standard curve constructed using values obtained from the standards. An average value can be determined for the unknown sample by plotting the value obtained on the standard curve. The calculations which are performed to determine unknown FPA quantitatively are based on conventional methodology. Counts in the tubes which contain zero FPA are set at 100% (defined as the B sub-zero closing). As FPA in the standard is increased, counts (defined as B closing) decreased in the precipitate as these counts are divided by the counts in the zero tube to give B/B sub-zero values. The B/B sub-zero values can be plotted against concentration of FPA on semi-log graph paper. The logit transformation of B/B zero and log of FPA concentration may be used to convert the curve to a straight line.

In some instances it may be desirable to provide a non-specific binding control buffer which does not contain any specific antibody. This control buffer may be used to ascertain the radiolabeled FPA not specifically separated from the reaction medium. These instances, the true bound tracer may be determined by subtracting the non-specific counts from all samples.

For use in carrying out the RIA methods of this invention, packaged test kits containing the necessary reagents and materials are provided. The package may have three or fewer separate components where there is provided a radiolabeled FPA reagent; a FPA antibody reagent specific to said FPA; and an anticoagulant reagent. Each of the reagents may be provided as separate components in the package to provide a three component package or one or more of the reagents may be combined to provide a package having fewer than three separate components. Test packages may also include in addition to the three or fewer components additional components, for instance, FPA reagents for preparation of standard and control samples, a second antibody reagent which is not specific to the FPA but which is specific to the FPA antibody, plasma pretreatment reagent, as well as apparatus for performing the tests, such as bottles for storing the reagents, vials for performing the tests and in certain instances for the storing reagents, e.g. control and standard samples. The entire package may be stored and shipped at ambient temperatures, and upon receipt by the user it may be stored at refrigerator temperature, e.g. 2° C. to 8° C. until ready for use.

The following examples will further illustrate the invention although it will be appreciated that the invention is not limited to these specific examples.

EXAMPLE 1

Reagents for use in a radioimmunoassay of Fibrinopeptide A are prepared as follows:

1. A fibrinopepetide A (FPA) I-125 is prepared containing approximately 6 nanograms N-tyrosyl FPA I 125 in a 0.05 M Tris buffer containing 0.1% disodium ethylene diamine tetraacetate, 0.2% equine albumin, 0.04% cycloheximide, 0.005% chloramphenicol, 0.584% sodium chloride, and 0.005% FD & C Yellow #5. The pH of this solution is 8.40±0.05. The solution contains less than 10 micro Ci I 125.

2. Fibrinopeptide A standards are prepared by making appropriate dilutions of pure fibrinopeptide A antigen in a 0.05 M Tris buffer (containing 0.133% weight to volume disodium ethylene diamine tetraacetate, 0.30% weight to volume equine albumin, 0.04% cycloheximide, 0.005% weight to volume chloramphenicol, 0.584% weight to volume sodium chloride and 33 KIU per milliliter aprotinin). The standards are equivalent to 0.0, 1.0, 2.0, 5.0, 10.0, 20.0, and 40.0 nanograms per milliliter.

3. Fibrinopeptide A quality control materials are prepared by adding pure fibrinopeptide A antigen in a Tris buffered protein solution (same as standards) at approximately concentrations of 1.3 and 8.0 nanograms per milliliter.

4. Fibrinopeptide A first antibody reagent is prepared from antisera which has been bled from a rabbit previously innoculated with a conjugated fibrinopeptide A-bovine serum albumin immunogen. The antiserum is diluted greater than 1:100 with 0.05 M Tris buffer containing 0.10% weight to volume equine albumin, 0.04% weight to volume cycloheximide, 0.005% weight to volume chloramphenicol, 0.0035% weight to volume FD &C Blue Dye #1, 0.584% weight to volume sodium chloride and 10 USP K units per milliliter heparin.

5. A polyethylene glycol second antibody reagent is prepared containing 6.5% weight to volume of polyethylene glycol having a molecular weight of 6,000–7,000 in 0.1 M sodium phosphate buffer containing preservatives. To the polyethylene glycol solution is added 1.5–5.0% volume to volume normal human serum and 2 to 4 milliliters per liter goat anti-rabbit gamma globulin antiserum.

6. A bentonite slurry is prepared by adding 75 milligram per milliliter bentonite to a 0.05 M TRIS buffer containing 0.20% weight to volume equine albumin, 0.04% cycloheximide, 0.005% chloramphenicol and 0.584% sodium chloride. The pH of this solution is 8.7.

7. A non-specific binding buffer is identical to the first antibody reagent except this does not contain anti-fibrinopeptide A antisera.

8. An anticoagulant solution is prepared to contain 4.0% weight to volume disodium ethylene diamine tetraacetate, 1000 KIU per milliliter aprotinin (Trasylol®), 0.3–0.6 milligram per milliliter of D-Phe-Pro-ArgCh$_2$Cl and 0.9% weight to volume sodium chloride. The pH of this solution is 4.5.

Preparation of Anticoagulant Sample Tubes:

Inject 0.5 ml anticoagulant using a gas tight syringe into a 5 ml evacuated blood collection tube. Tubes should be stored at 4° C. until used.

Blood Sample Collection and Preparation:

Collect blood by flawless venipuncture using a 20 gauge single sample needle. Remove tourniquet after needle has been inserted into vein. Collect 5 ml blood into evacuated tube which contains the proper anticoagulant. Thoroughly mix the blood and anticoagulant by inverting gently.

The samples should be centrifuged at 1000–1500×g for 20 minutes at 4° C. or RT as soon as possible after collection. Separate plasma from cells and store at −20° C. or lower temperature until assayed.

Plasma Sample Treatment:

Dispense 0.5 ml (500 μl) plasma into a 12×75 glass, polystyrene or polyethylene tube. Add 1.0 ml of the bentonite slurry which has been thoroughly mixed. Vortex and centrifuge at a minimum of 1200×g for 10 minutes. Carefully aspirate supernatant and transfer to clean tubes, taking precautions not to dislodge or aspirate any bentonite particles.

Assay Procedure:

1. Remove the required test components from the refrigerator and allow to equilibrate to room temperature (20°–26° C.).
2. Add 200 microliters of each of the 0.00, 1.00, 2.00, 5.00, 10.00, 20.00 and 40.00 ng/ml standards to a series of tubes. Add 200 μl of patient's treated samples to another series of tubes. A corresponding duplicate set of non-specific binding (NSB) tubes is prepared by adding 200 μl of the 0.00 ng/ml standard.
3. Dispense 100 μl of the Fibrinopeptide A I-125 Reaction Solution into all the tubes.
4. Gently vortex each tube for several seconds to insure thorough mixing.
5. Dispense 100 ul of the Fibrinopeptide A antibody solution into all tubes except the NSB tubes which will receive 100 μl of NSB buffer.
6. Gently vortex each tube for several seconds to insure thorough mixing.
7. Cover tubes and incubate for 40 to 120 minutes at room temperature (20°–26° C.).
8. Thoroughly mix the PEG-second antibody solution and dispense 1.0 ml to all tubes using the same order of addition and timing sequence that was used in dispensing the antibody solution in Step 5. Vortex vigorously for several seconds.
9. Centrifuge all tubes at 1200×g or greater for 20 minutes at room temperature.
10. Decant the contents of the tubes and discard the liquid. Allow tubes to drain on absorbent paper for at least 5 minutes. Tap the lip of the tube on a paper towel to absorb remaining liquid.

Each tube is then counted for radioactivity for a period sufficient to accumulate a minimum of 10,000 counts and the net counts per minute (cpm) of each concentration of standard and patient's sample are determined and recorded. The net cpm of each standard, patient, or control serum tube is divided by the average net cpm of the zero ng/ml standard tubes and multiplied by 100. The quotient represents the proportion of FPA I-125 bound to the antibody in the presence of FPA compared to the amount bound in the absence of FPA (percent $B/B_0$).

A standard curve is constructed by plotting the average percent $B/B_0$ of the duplicate values of each standard on the linear axis of semi-logarithmic graph paper as a function of the concentration of the standards in nanograms per milliliter. The average percent $B/B_0$ of the duplicate values of each patient's and control serum is determined, and the FPA concentration for the patient's or control serum's percent $B/B_0$ value from the standard curve is also determined. The FPA net cpm's and percent $B/B_0$ values are set forth below in Table 1.

TABLE 1

| FPA Standard (ng/ml) | Average Net CPM | % $B/B_0$ |
|---|---|---|
| 0.0 | 35,750 | 100.0 |
| 1.0 | 30,409 | 85.1 |
| 2.0 | 26,045 | 72.9 |
| 5.0 | 17,279 | 48.3 |
| 10.0 | 10,852 | 30.4 |
| 20.0 | 6,455 | 17.9 |
| 40.0 | 3,521 | 9.8 |

EXAMPLE II

Preliminary data on 35 normal subjects age 25 to 60 years gave values of 0.3 to 1.7 nanograms FPA per milliliter of plasma.

Intra-runs and inter-runs on multiple assays have shown coefficiencies of variation of less than 10%. Values as low as 0.1 nanogram per milliliter can be distinguished from the 0.0 nanogram per milliliter standard.

An accuracy study was performed on two separate plasma samples to which various amounts of pure fibrinopeptide A was added. The samples were assayed for fibrinopeptide A and the recovered values were compared to the expected values. The average recovery value was 100.8%.

An elevated fibrinopeptide A plasma sample (approximately 30 nanograms per milliliter) was serially diluted and assayed for fibrinopeptide A. The diluted sample recovered linearly throughout the standard curve.

The above data shows that the method is very accurate, sensitive, and reproducible at levels of fibrinopeptide A of 0.3 to 40.0 nanograms per milliliter.

What is claimed:

1. In a competitive radioimmunoassay method for determining the concentration of fibrinopeptide A in plasma wherein first, a sample of blood is collected, the thrombin in said sample is inhibited by an inhibiting amount of a thrombin inhibitor and plasma is separated from said sample, and second, a sample of said plasma is contacted under radioimmunoassay competitive binding conditions with a sufficient amount of an antibody to fibrinopeptide A and radioactively labelled fibrinopeptide A, thereafter, antibody bound fibrinopeptide A is separated from the unbound fibrinopeptide A and radioactivity measured, the improvement comprising using as the inhibitor for thrombin an inhibitor selected from the group consisting of D-phenylalanyl-L-propyl-L-N-[2(1-chloro-7-guanidoheptane-2-one)] the hydrochloric acid addition salt thereof; the hydroflouric acid addition salt thereof, the acetic acid addition salt thereof and the citric acid addition salt thereof.

2. A process according to claim 1 wherein the plasma is pretreated with bentonite.

3. A process according to claim 2 wherein a chelating agent in a chelating amount and an antiproteolytic agent in an antiproteolytic amount is present during the inhibition of thrombin by the inhibitor.

4. An anticoagulation reagent for the inhibition of thrombin for use in connection with the in vitro determination of fibrinopeptide A comprising an aqueous solution of (1) as an inhibitor for thrombin selected from the group consisting of D-phenylalanyl-L-propyl-L-N-[2(1-chloro-7-guanidoheptane-2-one)] the hydrochloric acid addition salt thereof; the hydroflouric acid addition salt thereof, the acetic acid addition salt thereof and the citric acid addition salt thereof (2) a chelating agent and (3) an antiproteolytic agent, said inhibitor, chelating agent and antiproteolytic agent each being present in an amount sufficient to bring about its intended function on addition to blood.

5. A reagent according to claim 4 wherein the chelating agent is selected from the group consisting of ethylenediaminetetracetic acid, ethylene glycol bis(B-amionoethyl ether)N,N,N',N'-tetracetic acid and sodium salts thereof.

6. A reagent according to claim 5 wherein the antiproteolytic agent is aprotinin.

7. A reagent according to claim 6 wherein the chelating agent is selected from the group consisting of ethylenediaminetetracetic acid, ethylene glycol bis(B-aminoethyl ether)N,N,N',N'-tetracetic acid and sodium salts thereof.

8. A test kit for the radioimmunoassay of the concentration of fibrinopeptide A in plasma which comprises a radiolabelled fibrinopeptide A reagent; a fibrinopeptide A antibody reagent; and an anticoagulant reagent of claim 4.

9. A kit according to claim 8 wherein additionally is present a second antibody reagent which is not specific to fibrinopeptide A but which is specific to the antibody for fibrinopeptide A.

10. A kit according to claim 9 which also includes pure fibrinopeptide A reagent standards and control samples.

11. A kit according to claim 9 wherein said reagents are provided in an aqueous solution having a pH of about 4 to about 10.

* * * * *